United States Patent
Girijavallabhan

(10) Patent No.: US 10,671,609 B2
(45) Date of Patent: Jun. 2, 2020

(54) METHODS AND APPARATUSES FOR FACILITATING COMPILATION OF MEASURE DATA

(71) Applicant: Change Healthcare Holdings, LLC, Nashville, TN (US)

(72) Inventor: Sarath Girijavallabhan, Nashua, NH (US)

(73) Assignee: Change Healthcare Holdings, LLC, Nashville, TN (US)

( * ) Notice: Subject to any disclaimer, the term of this patent is extended or adjusted under 35 U.S.C. 154(b) by 324 days.

(21) Appl. No.: 15/355,656

(22) Filed: Nov. 18, 2016

(65) Prior Publication Data

US 2018/0144002 A1    May 24, 2018

(51) Int. Cl.
*G06F 16/2455* (2019.01)
*G16H 15/00* (2018.01)
*G06F 16/2452* (2019.01)
*G06Q 50/26* (2012.01)

(52) U.S. Cl.
CPC ...... *G06F 16/2455* (2019.01); *G06F 16/2452* (2019.01); *G16H 15/00* (2018.01); *G06Q 50/26* (2013.01)

(58) Field of Classification Search
CPC ......... G06F 17/30477; G06F 17/30427; G06F 19/328; G06F 19/324; G06F 16/2455; G06Q 50/26; G16H 15/00
See application file for complete search history.

(56) References Cited

U.S. PATENT DOCUMENTS

| | | | |
|---|---|---|---|
| 7,333,999 B1* | 2/2008 | Njemanze | G06F 8/33 |
| 7,516,121 B2* | 4/2009 | Liu | G06F 16/2448 |
| 8,880,454 B2* | 11/2014 | Christie, IV | G06F 19/324 706/47 |
| 8,972,445 B2* | 3/2015 | Gorman | G06F 40/30 707/771 |
| 9,026,903 B1* | 5/2015 | Michael | G06F 17/2247 715/235 |
| 2007/0028222 A1* | 2/2007 | Meijer | G06F 8/43 717/140 |

(Continued)

OTHER PUBLICATIONS

HL7 Cross-Paradigm Specification: Clinical Quality Language, Relaese 1 (Year: 2016).*

(Continued)

*Primary Examiner* — Jean M Corrielus
(74) *Attorney, Agent, or Firm* — Alston & Bird LLP

(57) ABSTRACT

Embodiments are disclosed for facilitating the compilation of measure data. In the context of a method, an example embodiment includes generating, by configuration circuitry of an interpreter, at least one abstract syntax tree based on a CQL file containing measure logic and a CQL grammar file. This example embodiment of the method further includes converting, by the configuration circuitry, the at least one abstract syntax tree into at least one strongly-typed expression tree and storing the at least one strongly-typed expression tree in a memory. Finally, the example embodiment of the method may further include executing, by data evaluation circuitry of the interpreter, the at least one strongly-typed expression tree using retrieved user data. Corresponding apparatuses and computer program products are also provided.

19 Claims, 13 Drawing Sheets

(56) References Cited

U.S. PATENT DOCUMENTS

| | | | |
|---|---|---|---|
| 2008/0208625 A1 | 8/2008 | Joseph | |
| 2008/0215370 A1* | 9/2008 | Dent | G06F 21/6245 |
| | | | 705/3 |
| 2009/0328016 A1* | 12/2009 | Ng | G06F 8/427 |
| | | | 717/143 |
| 2011/0202370 A1 | 8/2011 | Green, III et al. | |
| 2011/0301982 A1 | 12/2011 | Green et al. | |
| 2012/0159459 A1* | 6/2012 | Turner | G06F 8/314 |
| | | | 717/138 |
| 2012/0174014 A1* | 7/2012 | Ash | G06F 19/3418 |
| | | | 715/771 |
| 2013/0006910 A1* | 1/2013 | Christie, IV | G06F 19/324 |
| | | | 706/47 |
| 2013/0006911 A1* | 1/2013 | Christie, IV | G06F 19/324 |
| | | | 706/47 |
| 2013/0006912 A1* | 1/2013 | Christie, IV | G06F 19/324 |
| | | | 706/47 |
| 2013/0263099 A1* | 10/2013 | Box | G06F 8/42 |
| | | | 717/144 |
| 2015/0186504 A1* | 7/2015 | Gorman | G06F 40/205 |
| | | | 707/752 |

OTHER PUBLICATIONS

Clinical Quality and Policy, Agency for healthcare research what is workflow, Rockville MD, Oct. 2010.*
Clinicians Quality Language (CQL) Training for measure implementers, Shanna Hartman, Jun. 22, 2016.*
Strongly Typed Genetic Programming, Montana et al., (Year: 2002).*
On the automated translational execution of the action language for foundational UML, Federico Ciccozzi (Year: 2016).*
Using OCL to navigate ASTs, Antoniol et al., (Year: 2003).*
Office Action for U.S. Appl. No. 15/355,656 dated Dec. 13, 2018.
Office Action for U.S. Appl. No. 15/355,656 dated Apr. 18, 2019.

* cited by examiner

METHODS AND APPARATUSES FOR FACILITATING COMPILATION OF MEASURE DATA

TECHNOLOGICAL FIELD

Example embodiments of the present invention relate generally to file conversion and execution and, more particularly, to methods and apparatuses for implementing an interpreter architecture for automatically converting measure logic from a first format to a second.

BACKGROUND

Historically, the components of measures have been expressed in a variety of ad hoc forms, primarily in written text. To gather and report measures to governmental agencies, service providers have had to manually develop executable code that can be used to query their proprietary database management systems and gather the necessary information. This approach is slow, cumbersome, and error-prone. Moreover, because the relevant measures requested by governmental agencies often change from year to year, the exercise has historically needed to be repeated periodically.

BRIEF SUMMARY

As will be described in greater detail below, example embodiments provide for the conversion of measure logic expressed in a file written in a new programming language, CQL (discussed below), into a strongly-typed expression tree that is thus in an executable form for a given service provider. By doing so, example embodiments can automatically determine the state of a user within a measure (e.g., whether they belong within the denominator and/or numerator) by executing the strongly-typed expression tree in connection with the corresponding user data stored by the service provider.

Example embodiments described herein avoid the need to manually hand-write executable code for each set of CQL-defined measure logic, which saves time and resources, while also eliminating the possibility of human error that has been unavoidable in the past. Moreover, embodiments described herein avoid the overhead of dealing with flat CQL files themselves, as described in greater detail below. Finally, embodiments that bifurcate the generation of strongly-typed expression trees from the run-time execution of the measure provide a mechanism that creates an executable and storable (e.g., persistable) expression tree in a first authoring/configuration stage, which in turn expedites the actual execution of the measure by avoiding the need for on-the-fly interpretation of a CQL file during a second run-time stage. Embodiments including such bifurcation provide yet another benefit, which is that they avoid common errors such as syntax errors, file-not-found errors, or the like that may be encountered when attempting to read and parse CQL files at run-time.

In a first example embodiment, a method is provided for facilitating the compilation of measure data. The method includes generating, by configuration circuitry of an interpreter, at least one abstract syntax tree based on a CQL file containing measure logic and a CQL grammar file, converting, by the configuration circuitry, the at least one abstract syntax tree into at least one strongly-typed expression tree, and storing the at least one strongly-typed expression tree in a memory.

In some embodiments, the method includes, for a particular abstract syntax tree of the at least one abstract syntax tree, pruning, by the configuration circuitry, non-pertinent information from each node of the particular abstract syntax tree, wherein non-pertinent information comprises information unrelated to node type or node value. In such embodiments, the step of converting the particular abstract syntax tree into a corresponding strongly-typed expression tree is performed after pruning all non-pertinent information from each node of the particular abstract syntax tree.

It will be understood that in some embodiments, converting a particular abstract syntax tree of the at least one abstract syntax tree into a corresponding strongly-typed expression tree includes evaluating, by the configuration circuitry, one or more nodes of the particular abstract syntax tree using a set of predefined mapping rules that define a correspondence between abstract syntax tree nodes and strongly-typed expression tree nodes, and creating, by the configuration circuitry, the corresponding strongly-typed expression tree, wherein the corresponding strongly-typed expression tree only includes nodes from the particular abstract syntax tree for which a correspondence to strongly-typed expression tree nodes is defined by the set of pre-defined mapping rules. In some such embodiments, the corresponding strongly-typed expression tree is structured as a prefix kind of tree.

In some embodiments, the method further includes retrieving the at least one strongly-typed expression tree from the memory, retrieving user data from a database management system; executing, by data evaluation circuitry of the interpreter, each of the at least one strongly-typed expression tree using the retrieved user data; and classifying, by the data evaluation circuitry, each particular user identified by the user data according to values returned from executing each of the at least one strongly-typed expression tree. In some such embodiments, executing a particular strongly-typed expression tree using the received user data includes initializing, by the data evaluation circuitry, an evaluation operation on a top node of the particular strongly-typed expression tree using data for each particular user identified by the user data. Moreover, in such embodiments, the evaluation operation of a particular node of the particular strongly-typed expression tree initiates an evaluation on all lower level nodes underneath the particular node of the particular strongly-typed expression tree.

It will be understood that the evaluation operation of a particular node may in some embodiments include steps of: evaluating if one or more lower-level nodes exist; in an instance in which one or more lower-level nodes do not exist, returning a value associated with the particular node; and in an instance in which at least one lower level node exists, initializing an evaluation operation of each lower level node, receiving returned values from the evaluation operations of each lower level node, determining an operation represented by the particular node, performing the operation using the returned values from the evaluation operation initialized on each lower level node, and returning a value produced by performing the operation.

In another example embodiment, an apparatus is provided for facilitating the compilation of measure data. The apparatus includes at least one processor and at least one memory storing computer-executable instructions, that, when executed by the at least one processor, cause the apparatus to generate at least one abstract syntax tree based on a CQL file containing measure logic and a CQL grammar file, convert the at least one abstract syntax tree into at least one strongly-typed expression tree, and store the at least one strongly-typed expression tree in a memory.

In some embodiments of the apparatus, the computer-executable instructions, when executed by the at least one processor, further cause the apparatus to, for a particular abstract syntax tree of the at least one abstract syntax tree, prune non-pertinent information from each node of the particular abstract syntax tree, wherein non-pertinent information includes information unrelated to node type or node value. In such embodiments, the computer-executable instructions, when executed by the at least one processor, cause the apparatus to convert the particular abstract syntax tree into a corresponding strongly-typed expression tree after pruning all non-pertinent information from each node of the particular abstract syntax tree.

In some such embodiments, the computer-executable instructions, when executed by the at least one processor, cause the apparatus to convert a particular abstract syntax tree of the at least one abstract syntax tree into a corresponding strongly-typed expression tree by causing the apparatus to evaluate one or more nodes of the particular abstract syntax tree using a set of predefined mapping rules that define a correspondence between abstract syntax tree nodes and strongly-typed expression tree nodes, and create the corresponding strongly-typed expression tree, wherein the corresponding strongly-typed expression tree only includes nodes from the particular abstract syntax tree for which a correspondence to strongly-typed expression tree nodes is defined by the set of predefined mapping rules. In this regard, it will be understood that the corresponding strongly-typed expression tree may in some embodiments be structured as a prefix kind of tree.

In some embodiments of the apparatus, the computer-executable instructions, when executed by the at least one processor, further cause the apparatus to retrieve the at least one strongly-typed expression tree from the memory, retrieve user data from a database management system, execute each of the at least one strongly-typed expression tree using the retrieved user data, and classify each particular user identified by the user data according to values returned from executing each of the at least one strongly-typed expression tree.

In some such embodiments, the computer-executable instructions, when executed by the at least one processor, cause the apparatus to execute the particular strongly-typed expression tree using the received user data by causing the apparatus to initialize an evaluation operation on a top node of the particular strongly-typed expression tree using data for each particular user identified by the user data, in which case the evaluation operation of any particular node of the particular strongly-typed expression tree initiates an evaluation on all lower level nodes underneath the particular node of the particular strongly-typed expression tree. In this regard, the evaluation operation of a particular node may include the steps of: evaluating if one or more lower-level nodes exist; in an instance in which one or more lower-level nodes do not exist, returning a value associated with the particular node; and in an instance in which at least one lower level node exists, initializing evaluation operations of each lower level node, receiving returned values from the evaluation operations of each o lower level node, determining an operation represented by the particular node, performing the operation using the returned values from the evaluation operation initialized on each lower level node, and returning a value produced by performing the operation.

In yet another example embodiment, a computer program product comprising at least one non-transitory computer-readable storage medium is provided for facilitating the compilation of measure data. The at least one non-transitory computer-readable storage medium stores computer-executable instructions that, when executed, cause an apparatus to generate at least one abstract syntax tree based on a CQL file containing measure logic and a CQL grammar file, convert the at least one abstract syntax tree into at least one strongly-typed expression tree, and store the at least one strongly-typed expression tree in a memory.

In some embodiments of the computer program product, the computer-executable instructions, when executed, further cause the apparatus to, for a particular abstract syntax tree of the at least one abstract syntax tree, prune non-pertinent information from each node of the particular abstract syntax tree, wherein non-pertinent information includes information unrelated to node type or node value. In such embodiments, the computer-executable instructions, when executed, cause the apparatus to convert the particular abstract syntax tree into a corresponding strongly-typed expression tree after pruning all non-pertinent information from each node of the particular abstract syntax tree.

In some embodiments of the computer program product, the computer-executable instructions, when executed, cause the apparatus to convert a particular abstract syntax tree of the at least one abstract syntax tree into a corresponding strongly-typed expression tree by causing the apparatus to evaluate one or more nodes of the particular abstract syntax tree using a set of predefined mapping rules that define a correspondence between abstract syntax tree nodes and strongly-typed expression tree nodes; and create the corresponding strongly-typed expression tree, wherein the corresponding strongly-typed expression tree only includes nodes from the particular abstract syntax tree for which a correspondence to strongly-typed expression tree nodes is defined by the set of predefined mapping rules.

In some such embodiments, the corresponding strongly-typed expression tree is structured as a prefix kind of tree.

In some embodiments of the computer program product, the computer-executable instructions, when executed, further cause the apparatus to retrieve the at least one strongly-typed expression tree from the memory, retrieve user data from a database management system, execute each of the at least one strongly-typed expression tree using the retrieved user data, and classify each particular user identified by the user data according to values returned from executing each of the at least one strongly-typed expression tree. In some example embodiments, the computer-executable instructions, when executed, cause the apparatus to execute the particular strongly-typed expression tree using the received user data by causing the apparatus to initialize an evaluation operation on a top node of the particular strongly-typed expression tree using data for each particular user identified by the user data, in which case the evaluation operation of any particular node of the particular strongly-typed expression tree initiates an evaluation on all lower level nodes underneath the particular node of the particular strongly-typed expression tree. In this regard, the evaluation operation of a particular node comprises: evaluating if one or more lower-level nodes exist; in an instance in which one or more lower-level nodes do not exist, returning a value associated with the particular node; and in an instance in which at least one lower level node do exists, initializing evaluation operations of each lower level node, receiving returned values from the evaluation operations of each lower level node, determining an operation represented by the particular node, performing the operation using the returned values from the evaluation operation initialized on each lower level node, and returning a value produced by performing the operation.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which are not necessarily drawn to scale.

FIG. 2A illustrates an example of a partial abstract syntax tree generated based on specific measure logic, in accordance with some example embodiments described herein.

FIG. 2B illustrates an example of a strongly-typed expression tree generated based on the partial abstract syntax tree of FIG. 2A, in accordance with some example embodiments described herein.

FIG. 2C illustrates an abstract syntax tree generated based on measure logic from a CQL file, in accordance with some example embodiments described herein.

FIG. 6 illustrates example code for converting an abstract syntax tree into a strongly-typed expression tree, in accordance with some example embodiments described herein.

DETAILED DESCRIPTION

Figure 1:
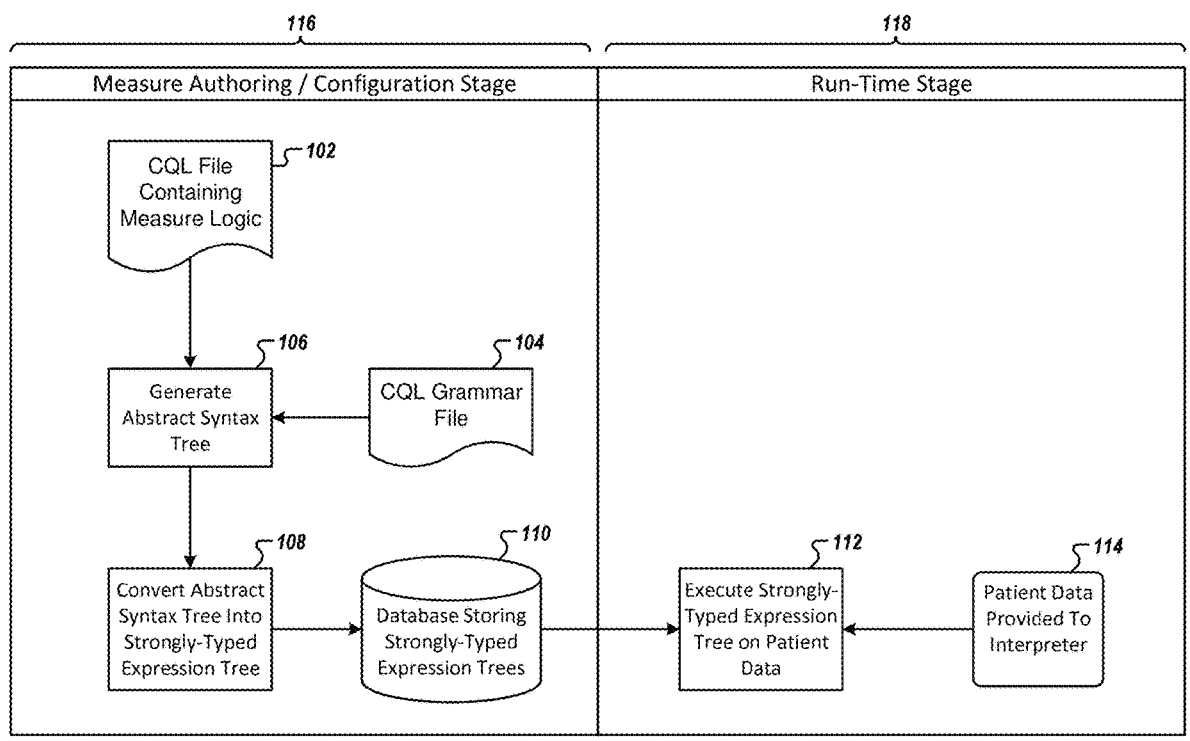
FIG. 1 illustrates a schematic diagram of an example CQL interpreter architecture, in accordance with some example embodiments described herein.

Some embodiments of the present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention.

Overview

After enactment of the American Recovery and Reinvestment Act of 2009 (ARRA), the Centers for Medicare and Medicaid Services (CMS) began requesting the provision of clinical quality measures (CQMs) from service providers and hospitals. A CQM, or measure, is a mechanism used for assessing the degree to which a provider competently and safely delivers clinical services that are appropriate for the patient in an optimal timeframe. These measures are used by CMS to evaluate many aspects of patient care, such as health outcomes, clinical processes, patient safety, efficient use of healthcare resources, care coordination, patient engagement, population and public health, and adherence to clinical guidelines. To incentivise healthcare providers to collect relevant data and provide measures for evaluation, the ARRA authorized CMS to provide incentive payments to qualified professionals and hospitals in exchange for the provision of these measures. Because of the large volume of patients covered by Medicare and Medicaid, production of measures is of significant importance to healthcare providers, hospitals, and health insurers alike.

Measures generally include three principle components: (1) an initial patient population; (2) a denominator; and (3) a numerator. The initial patient population for a measure is the group of patients that the measure itself is designed to address (e.g., patients having diabetes). The denominator for the measure is a subset of the initial patient population, although it may in some instances be equal to the initial patient population (e.g., this may be some subset of the patients having diabetes or all of them). The numerator is a subset of the denominator for whom a particular process or outcome of care occurs (e.g., the subset of the denominator who have had a blood test every six months).

Recently, CMS has begun expressing measure logic in a new language called Clinical Quality Language (CQL) and designed by Health Level Seven® (HL7). The aim of this shift was to express measure logic in a consistent and rigorous manner. HL7 has published a CQL grammar that can be used to parse CQL measure logic so that providers can understand the components of a given measure. Although CQL has been adopted by CMS for internal consistency purposes, the inventor has identified an opportunity to improve upon historical methods for collecting measure data for reporting to CMS. Because CQL is a new language, no existing software or tool can interpret CQL logic and convert it into a form that can be used to query database management systems. And because measure logic was previously never provided in a homogeneous format, a need for such a tool had never existed previously. However, with the now-consistent provision of measures in CQL form, example embodiments described herein provide a new mechanism for improving the efficiency, speed, and accuracy of measure-reporting by healthcare providers.

As mentioned above, traditional approaches for the collection and reporting of measure data have suffered from numerous drawbacks, largely related to the need to manually program code to gather the required information, which has been exacerbated by the fact that the measures themselves have changed on a periodic basis.

But because CMS has recently begun expressing measure logic using CQL files, the inventor has identified an opportunity to improve upon historical methods for collecting measure data for reporting to CMS. CQL is a new language, so no existing software or tool can interpret CQL logic and convert it into a form that can be used to query database management systems. And because measure logic was previously never provided in a homogeneous format, a need for such a tool had never existed previously.

FIG. 1 illustrates an example CQL interpreter architecture for converting logic expressed in a CQL file into a strongly-typed expression tree and for executing the strongly-typed expression tree on patient data. Initially, a measure 102 is retrieved in CQL (from CMS or another source). As noted previously, HL7 has published a CQL grammar, shown here as CQL grammar file 104. As shown at box 106, the apparatus embodying the interpreter of an example embodiment utilizes a parser generator to create one or more abstract syntax trees from the CQL file 102 and a CQL grammar file 104. In some embodiments, each abstract syntax tree is generated using Another Tool For Language Recognition (ANTLR). As shown at box 108, the apparatus generates, from the abstract syntax tree, a strongly-typed expression tree. Finally, the apparatus stores the strongly-typed expression tree representing the measure logic in a database 110. As shown at box 112, each strongly-typed expression tree can then be executed on particular patient data 114, and doing so for all strongly-typed expression trees generated based on the CQL file 102 generates an understanding of a patient's place within the measure described in the CQL file 102.

It should be noted that the components and operations illustrated in the CQL interpreter architecture shown in FIG. 1 can be implemented in a bifurcated manner. In this regard, the generation of a strongly-typed expression tree can be performed in a measure-authoring (or configuring) stage 116, while the actual execution of a given strongly-typed expression tree on patient data can then occur in a separate run-time stage 118. However, in other embodiments, it is conceivable that all of the operations are performed at run-time, such that the CQL file 102 is converted on-the-fly into a set of abstract syntax trees, which are immediately executed using patient data.

By following this process, example embodiments can automatically determine the state of a patient within a measure (e.g., whether they belong within the denominator and/or numerator) by executing the corresponding strongly-typed expression trees in connection with the corresponding patient data stored by the healthcare provider. Executing each strongly-typed expression tree on all patient data thereby enables the creation of a complete dataset for reporting to CMS, which in turn facilitates subsequent collection of any incentive or high-performance awards from CMS.

Accordingly, using the interpreter architecture described in connection with FIG. 1, example embodiments facilitate the reporting of measure data to CMS while avoiding the need to manually hand-write executable code for each set of CQL-defined measure logic. Example embodiments thus save time and resources, while also eliminating the possibility of human error that has been unavoidable in the past when CQL form was not used to provide measure logic. Moreover, example embodiments avoid the overhead of dealing with flat CQL files themselves, as mentioned above. Finally, embodiments that bifurcate the generation of strongly-typed expression trees from the run-time execution of the measure provide a mechanism that creates an executable and storable (e.g., persistable) expression tree in a first authoring/configuration stage, which in turn expedites the actual execution of the measure by avoiding the need for on-the-fly interpretation of a CQL file during a second run-time stage, and avoids common errors such as syntax errors, file-not-found errors, or the like that may otherwise be encountered when attempting to read and parse CQL files at run-time.

System Architecture

Methods, apparatuses, and computer program products of the present invention may be embodied by any of a variety of devices. Example embodiments may include a plurality of networked devices operating in a distributed system. In this regard, it will be understood that the term "distributed system" refers to a plurality of networked devices in which some components are shared among the devices. Whether or not the invention is implemented using a distributed system or not, example devices that may host the interpreter architecture may comprise any of a variety of fixed terminals, such as desktop computers, mainframe devices, kiosks, or the like. Similarly, example devices may also comprise any of a variety of mobile terminals, such as a portable digital assistant (PDA), mobile telephone, smartphone, laptop computer, tablet computer, or any combination of the aforementioned devices.

Figure 3:
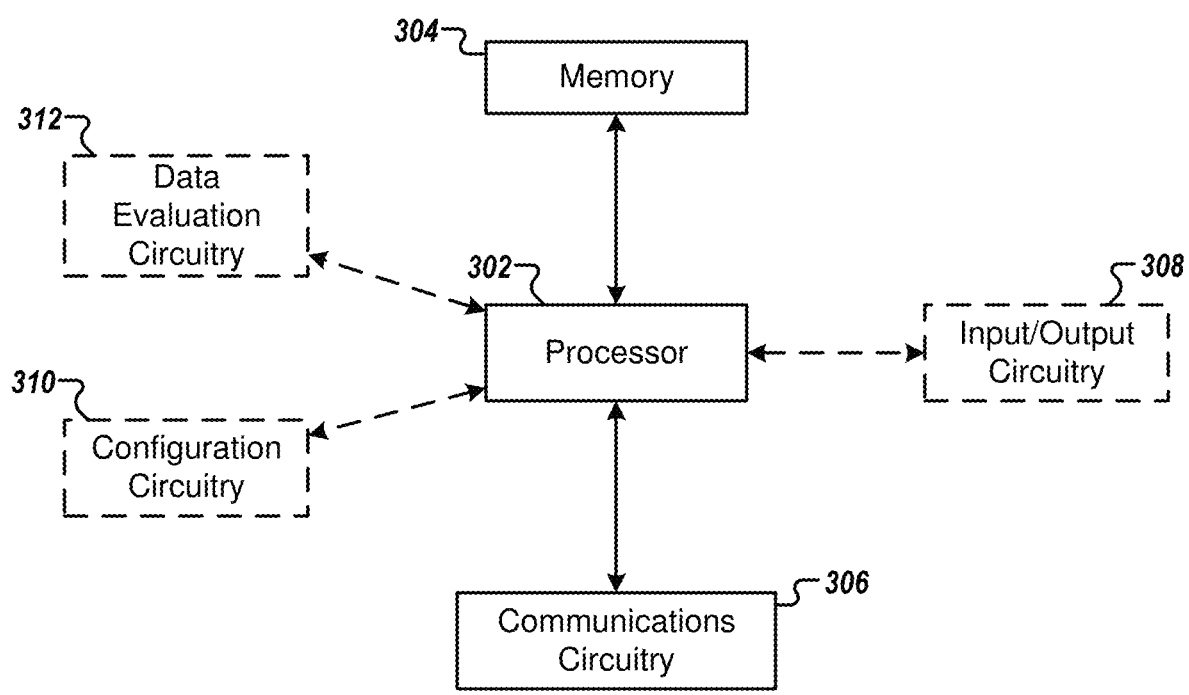
FIG. 3 illustrates a schematic block diagram of example circuitry embodying a networked device that may perform operations in accordance with some example embodiments described herein.

Turning to FIG. 3, an example apparatus 300 is illustrated that may represent a basic set of components of a given intepreter that may be configured to perform the operations described herein. The apparatus 300 may include a processor 302, a memory 304, and communications circuitry 306. The apparatus may further include input/output circuitry 308 that facilitates user interaction, configuration circuitry 310 for generating a strongly-typed expression tree from a CQL file and the CQL grammar, and data evaluation circuitry 312 for generating measure data using a strongly-typed expression tree and patient data (for eventual reporting to CMS). The apparatus 300 may be configured to execute the operations described below in connection with FIGS. 4, 5, 7, and 8. Although these components 302-312 are described with some functional descriptors, it should be understood that the particular implementations necessarily include the use of particular hardware. It should also be understood that certain of these components 302-312 may include similar or common hardware. For example, the configuration circuitry 310 may leverage use of the processor 302, memory 304, or communications circuitry 306, to perform its associated functions, and duplicate hardware is not required for the distinct components of the apparatus 300 (although embodiments using duplicated hardware are also contemplated herein). The use of the term "circuitry" as used herein with respect to components of the apparatus therefore includes particular hardware configured to perform the functions associated with the particular circuitry described herein. Of course, while the term "circuitry" should be understood broadly to include hardware, in some embodiments, circuitry may also include software for configuring the hardware components of the apparatus 300.

In some embodiments, the processor 302 (and/or coprocessor or any other processing circuitry assisting or otherwise associated with the processor) may be in communication with the memory 304 via a bus for passing information among components of the apparatus. The processor 302 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 302 may be configured to execute instructions stored in the memory 304 or otherwise accessible to the processor. Alternatively or additionally, the processor may be configured to execute hard-coded functionality. As such, whether configured by hardware or software methods, or by a combination of hardware with software, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the memory 304 may be non-transitory and may include, for example, one or more volatile and/or non-volatile memories. In other words, for example, the memory may be an electronic storage device (e.g., a computer readable storage medium). The memory 304 may be configured to store information, data, content, applications, instructions, or the like, for enabling the apparatus to carry out various functions in accordance with example embodiments contemplated herein.

The communications circuitry 306 may be any means such as a device or circuitry embodied in either hardware or a combination of hardware and software that is configured to receive and/or transmit data from/to a network and/or any other device, circuitry, or module in communication with the apparatus 300. In this regard, the communications circuitry 306 may include, for example, a network interface for enabling communications with a wired or wireless communication network. For example, the communications circuitry 306 may include one or more network interface cards, antennae, buses, switches, routers, modems, and supporting hardware and/or software, or any other device suitable for enabling communications via a network. Additionally or alternatively, the communication interface 306 may include the circuitry for interacting with the antenna(s) to cause transmission of signals via the antenna(s) or to handle receipt of signals received via the antenna(s). These signals may be transmitted by the apparatus 300 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols.

In some embodiments, the apparatus 300 may include input/output circuitry 308 that may, in turn, be in communication with processor 302 to provide output to a user and, in some embodiments, to receive an indication of user input. The input/output circuitry 308 may comprise a user interface and may include a display that may include a web user interface, a mobile application, a client device, or the like. In some embodiments, the input/output circuitry 308 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 104, and/or the like).

In addition, the apparatus 300 may also comprise configuration circuitry 310, which includes hardware components designed for generating one or more strongly-typed expression tree from a CQL file and the CQL grammar. The configuration circuitry 310 may utilize processor 302, memory 304, or any other hardware component included in the apparatus 300 to perform the operations described in connection with FIGS. 4 and 5 below. The configuration circuitry 310 may further utilize communications circuitry 306 to X.

The configuration circuitry 310 may utilize processing circuitry, such as the processor 302, to facilitate performance of its various operations, and may utilize memory 304 to store instructions that, when executed, cause the configuration circuitry 310 to perform its various operations and to store strongly-typed expression trees generated by the configuration circuitry 310. It should be appreciated that, in some embodiments, the configuration circuitry 310 may include a separate processor, specially configured field programmable gate array (FPGA), or application specific interface circuit (ASIC) to perform the above-described functions. In this fashion, the configuration circuitry 310 is therefore implemented using hardware components of the apparatus configured by either hardware or software for implementing these planned functions.

In addition, the apparatus 300 may also comprise data evaluation circuitry 312, which includes hardware components designed for applying measure logic to patient data specifically through the use of strongly-typed expression trees. The data evaluation circuitry 312 may utilize processor 302, memory 304, or any other hardware component included in the apparatus 300 to perform the operations described in connection with FIGS. 7 and 8 below. The data evaluation circuitry 312 may further utilize communications circuitry 306 to transmit a measure report to CMS, as illustrated in operation 412 of FIG. 4 below.

The data evaluation circuitry 312 may utilize processing circuitry, such as the processor 302, to facilitate performance of its various operations, and may utilize memory 304 to store instructions that, when executed, cause the data evaluation circuitry 312 to perform its various operations and store patient classification data generated by the data evaluation circuitry 312. It should be appreciated that, in some embodiments, the data evaluation circuitry 312 may include a separate processor, specially configured field programmable gate array (FPGA), or application specific interface circuit (ASIC) to perform the above-described functions. In this fashion, the data evaluation circuitry 312 is therefore implemented using hardware components of the apparatus configured by either hardware or software for implementing these planned functions.

As described above and as will be appreciated based on this disclosure, example embodiments of the interpreter contemplated herein may be implemented by apparatus 300. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

It should be appreciated, with respect to certain devices embodied by apparatus 300 as described in FIG. 3, computer program instructions and/or other type of code may be loaded onto a computer, processor or other programmable apparatus's circuitry to produce a machine, such that the computer, processor other programmable circuitry that execute the code on the machine create the means for implementing various functions described herein.

Having described specific components of example apparatus 300, example embodiments of the present invention are described below in connection with a series of flowcharts.

Operations for Generating Strongly-Typed Expression Trees

Figure 4:
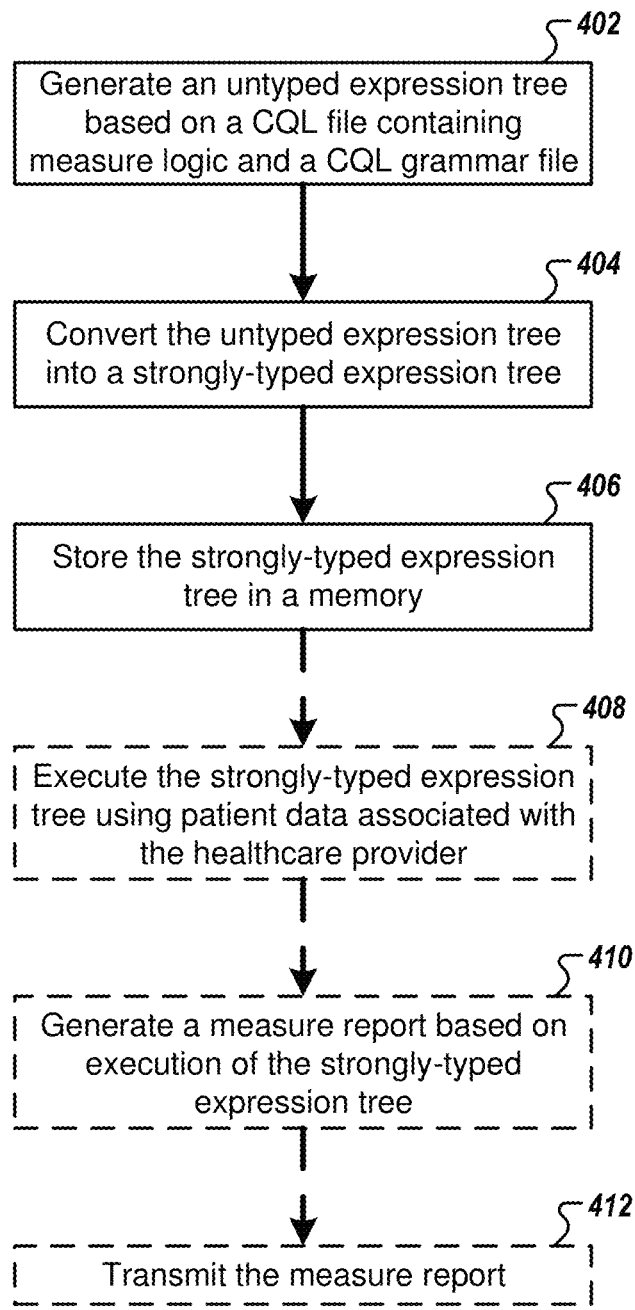
FIG. 4 illustrates a flowchart describing example operations for facilitating the compilation of measure data regarding one or more patients of a healthcare provider, in accordance with some example embodiments described herein.
Figure 5:
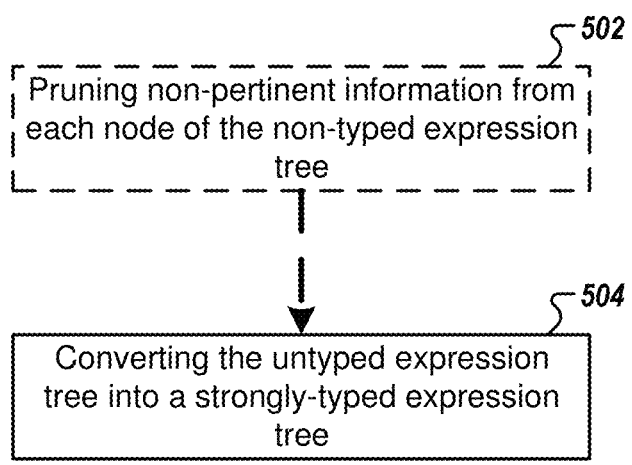
FIG. 5 illustrates a flowchart describing example operations for converting an abstract syntax tree into a strongly-typed expression tree, in accordance with some example embodiments described herein.

Turning to FIGS. 4 and 5, flowcharts are illustrated that contain operations for generating executable strongly-typed expression trees representing CQL measure logic. The operations illustrated in FIGS. 4 and 5 may, for example, be performed by, with the assistance of, and/or under the control of an interpreter embodied apparatus 300, and more particularly through the use of one or more of processor 302, memory 304, communications circuitry 306, input/output circuitry 308, configuration circuitry 310, or data evaluation circuitry 312.

Turning first to FIG. 4, example operations are provided for facilitating the compilation of measure data regarding one or more patients of a healthcare provider, in accordance with example embodiments described herein.

As illustrated in operation 402, the apparatus 300 includes means, such as configuration circuitry 310 or the like, for generating an abstract syntax tree based on a CQL file containing measure logic and the CQL grammar file. It should be understood that each abstract syntax tree is generated based on a corresponding statement from the CQL file. Accordingly, it may often be the case that multiple abstract syntax trees can be generated from a single CQL file when, as may occur frequently, multiple statements are contained in the CQL file. For ease of explanation, however, the following discussion relating to operations 404 and 406 describe utilization of a single abstract syntax tree generated from the CQL file, despite the fact that more abstract syntax trees may be generated and thus required to fully evaluate the entirety of the measure logic represented by the CQL file. It will further be appreciated that the CQL file may be retrieved in some fashion from CMS or another source endorsed by CMS. Because CMS has plans to publicly release a version of their Measure Authoring Tool (MAT) that will produce CQL files, the CQL file may in some embodiments be retrieved by an author who is not a source endorsed by CMS. Similarly, the CQL grammar file, originally generated by HL7, may be either locally stored ahead of time (e.g., in memory 304 or the like) or may be retrieved upon commencement of the procedure illustrated in FIG. 4. In any event, one having ordinary skill in the art would understand that it is possible to generate the abstract syntax tree based on the CQL file containing the measure logic provided that the CQL grammar file is also used. Generation of the abstract syntax tree may in some embodiments be performed using ANTLR, although other parser generators may be used in other embodiments. In this regard, ANTLR is a free and publicly available tool that can read in a given file, and based on a given grammar, generate a corresponding expression tree. The abstract syntax tree will depend on the grammar. Notably, using ANTLR or any other parser generator, it should be understood that the CQL grammar is very non-uniform. As a result, while it may conceivably be possible to develop an interpreter based directly on the abstract syntax tree, it is easier for the purposes of readability, expression tree persistence, and execution to transform the abstract syntax tree into a strongly-typed, pre-fix operation kind of expression tree.

To illustrate this concept, consider the following line of CQL measure logic:

define InDemographic:

AgeInYearsAt(start of MeasurementPeriod)>=2 and

AgeInYearsAt(start of MeasurementPeriod)<18

Figure 2A:
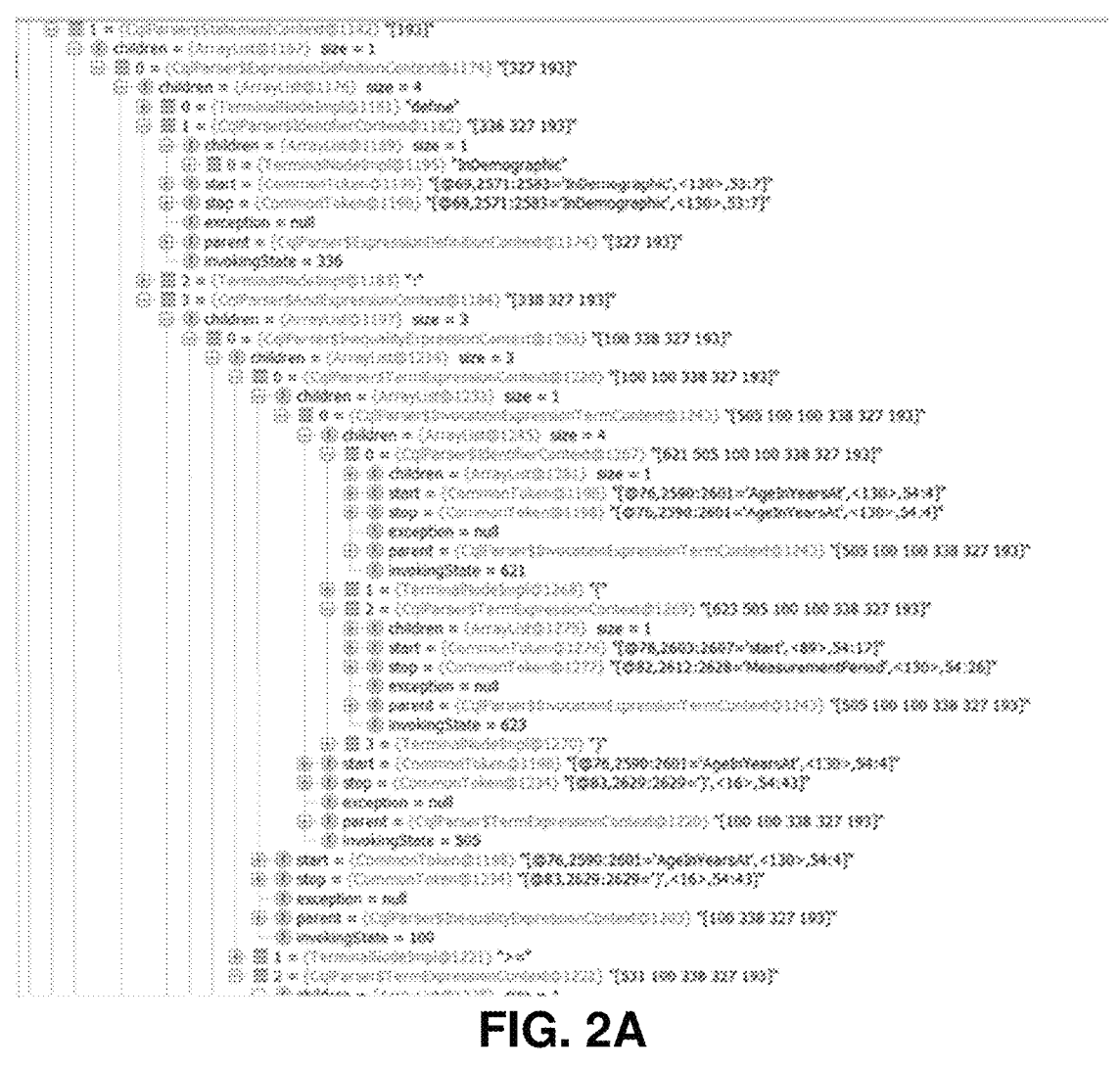

A fraction of the abstract syntax tree corresponding to this CQL measure logic is shown in FIG. 2A, while a corresponding fraction of a strongly typed expression tree is illustrated in FIG. 2B.

As illustrated in operation 404, the apparatus 300 includes means, such as configuration circuitry 310 or the like, for converting the abstract syntax tree into a strongly-typed expression tree of this nature. Both the abstract syntax tree and the strongly-typed executable expression tree essentially convey the same relevant information. The main difference between the two, beyond the addition of strong typing itself, is that extra layers of nesting and other non-pertinent nodes and node data in the abstract syntax tree are removed from the strongly-typed expression tree. This conversion to a strongly-typed executable one is done by a mapping exercise, as described in greater detail below in connection with FIG. 5.

The mapping exercise is an effort to create a tree-like structure depending on the corresponding abstract syntax tree structure. The operations illustrated in FIG. 5 provide a recursive way to generate the strongly-typed expression tree. In this regard, an operation in the abstract syntax tree, which may be represented as multiple nested levels, is converted into a strongly-typed pre-fix operation kind of tree. This strongly typed tree may also contain nested operations (as shown in FIG. 2F), but the tree should be constructed in such a way that every node in the tree is either an operand value for its parent, or should itself be an operation which can be evaluated to yield an operand value for the parent.

Each node in the strongly-typed tree is implemented as a class. The constructor of the class accepts as parameters the operands needed to perform the operation of the class. The class also has an "evaluate" function that will perform one of two operations: (1) if the operation of the class can be performed with the given operands, then the result is computed (e.g., by computing the sum of two integers passed in to an "ADD" class), but (2) if the operands are operations themselves, then the evaluate function will call the evaluate function of those operations. This process then continues until an operation can actually be performed to compute a result, as described in (1) above. Subsequently, the result from this operation is passed back to the evaluate function higher up in the calling stack. This evaluate function is described in greater detail below in connection with FIG. 8.

As an example, consider the following simple expression:

(3+5)>5 OR (1+2)<9

This expression will be represented by the strongly-typed tree shown in FIG. 2F. Each operation shown in a rectangular box is a class of type OR, GREATER, LESS, or LITERAL. All have an "evaluate" function that will either return a result of performing the corresponding operation on the operands, or will call the "evaluate" function of each sub-operation.

Each statement clause in a CQL file will thus have a corresponding strongly-typed expression tree. The evaluation of the tree is not done in the authoring/configuration step, because the last stage in this step is to save a collection of these trees into the database so that it can be retrieved on demand and executed based on patient data, as illustrated in connection with operation 406.

Turning next to operation 406, the apparatus 300 includes means, such as memory 304 or the like, for storing the strongly-typed expression tree. In some embodiments, the strongly-typed expression tree may be stored in association with metadata describing the related CQL measure logic and other identifying information that can be used to facilitate subsequent retrieval of the strongly-typed expression tree. In some embodiments, storage of the strongly-typed expression tree may be within a database of strongly-typed expression trees that can be accessed in a subsequent run-time stage for quick and efficient execution. In other embodiments, however, the storage may be in the database or in temporary storage for subsequent execution in substantially real-time. Accordingly, the interpreter can be considered to have two main stages, as shown in the architecture previously described in connection with FIG. 1. The first stage is an authoring or configuration-time stage, and encompasses operations 402-406. These operations take in the CQL file and convert it into a strongly-typed, pre-fix operation kind of executable expression tree. Technically, these operations can be performed at run-time. But operation 406 enables the strongly-typed expression tree to be persisted into the database, as shown in the architecture diagram in FIG. 1. By doing this, the second component of the interpreter can read in and execute the expression tree more quickly on the patient data, thereby speeding up the whole process.

The second stage is a run-time component that encompasses operation 408 below. It should be understood, however, that all of these operations can be done at run-time if desired, although in many embodiments it would be preferable to pre-calculate the one or more strongly-typed expression trees corresponding to each CQL file and store them in a database so that they can be quickly executed on the patient data in a separate run-time set of operations. This bifurcation typically speeds up the execution time of the run-time stage. In any event, once stored, the strongly-typed expression tree remains dormant until used again in optional operation 408.

As illustrated in optional operation 408, the apparatus 300 may also include means, such as data evaluation circuitry 312 or the like, for executing the strongly-typed expression tree(s) using patient data associated with the healthcare provider. This optional operation is described in greater detail in connection with FIGS. 7 and 8 below.

As illustrated in optional operation 410, the apparatus 300 may also include means, such as data evaluation circuitry 312 or the like, for generating a measure report based on execution of the strongly-typed expression tree. As detailed below in connection with FIGS. 7 and 8, execution of the strongly-typed expression tree results in classification of each of the patients based on the measure logic originally provided in the CQL file. This classification establishes where the patient falls in the measure based on the measure components identified in the strongly-typed expression tree. For instance, the patient may be determined to be within the initial patient population, in the denominator of the measure but not in the numerator of the measure, in both the denominator and numerator of the measure, or outside both the denominator and numerator due to an exception. Accordingly, generating the measure report thus entails the collating into a single document of classification data regarding every patient in the patient data retrieved regarding the healthcare provider, thus painting a global picture of the measure as it relates to the healthcare provider's patient set. Following generation of the measure report, the procedure advances to optional operation 412.

As illustrated in optional operation 412, the apparatus 300 may also include means, such as communications circuitry 306 or input/output circuitry 308 for transmitting the measure report to CMS. As described previously, this transmission may facilitate the distribution of an incentive or high-performance award from CMS based on the nature of the measure data reported.

It should be understood that operations 408, 410, and 412 are optional insofar as they illustrate operations that need not necessarily occur in a single instance. While operations 402-406 illustrate the generation and storage of a strongly-typed expression tree based on a CQL file and the CQL grammar, optional operations 408, 410, and 412 describe operations that ultimately utilize that strongly-typed expression tree to collect and report measure data to CMS.

Turning next to FIG. 5, example operations are described for converting an abstract syntax tree into a strongly-typed expression tree, in accordance with example embodiments described herein.

As illustrated in optional operation 502, the apparatus 300 includes means, such as configuration circuitry 310 or the like, for pruning non-pertinent information from each node of the abstract syntax tree. It should be understood that pertinent information consists of type information for a given node (e.g., TermExpression type, etc.). Other pertinent information may be any string value like "or", or a numerical value like "5", or a Boolean value like "false". FIG. 2C shows an example of a cleaned-up un-typed expression tree for the following expression:

(3+5)>5 or false.

Figure 2D:
FIG. 2D provides a pictorial representation of the abstract syntax tree shown in FIG. 2C, in accordance with some example embodiments described herein.

In turn, FIG. 2D illustrates a pictorial representation of the structure shown in FIG. 2C.

Operation 502 is described as optional for two reasons. First, it need not be performed on an abstract syntax tree because it may be a predicate precursor step to generation of the abstract syntax tree itself. Thus, in some embodiments it is only optional insofar as it does not necessarily occur after generation of the abstract syntax tree. In other embodiments, however, the created abstract syntax tree may not need pruning, and in such situations operation 502 may not be performed at all.

Figure 2E:
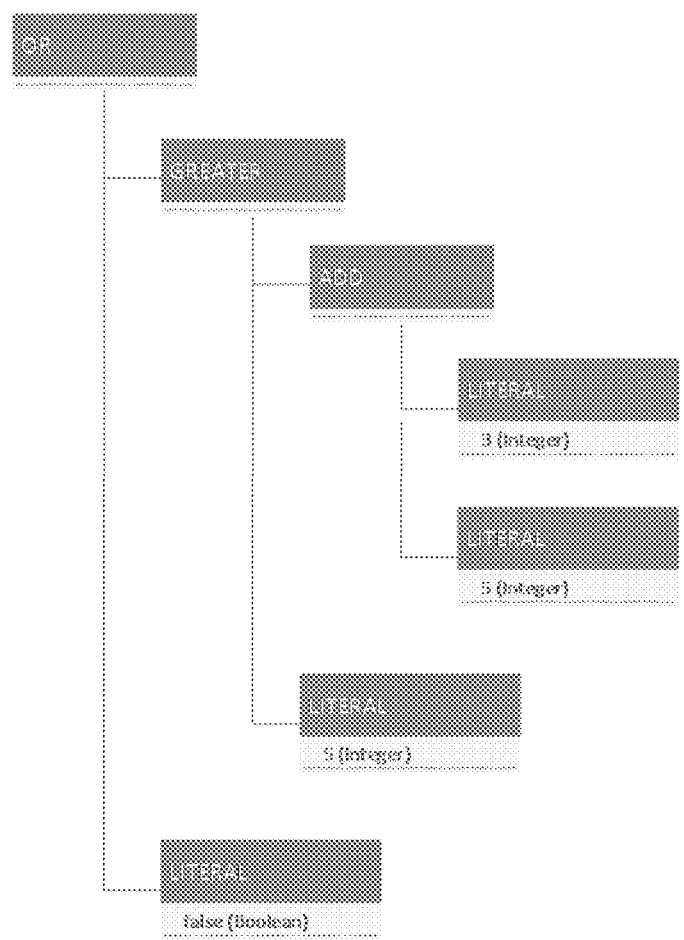
FIG. 2E illustrates an example of a strongly-typed expression tree corresponding to the abstract syntax tree illustrated in FIGS. 2A and 2B, in accordance with some example embodiments described herein.
Figure 2F:
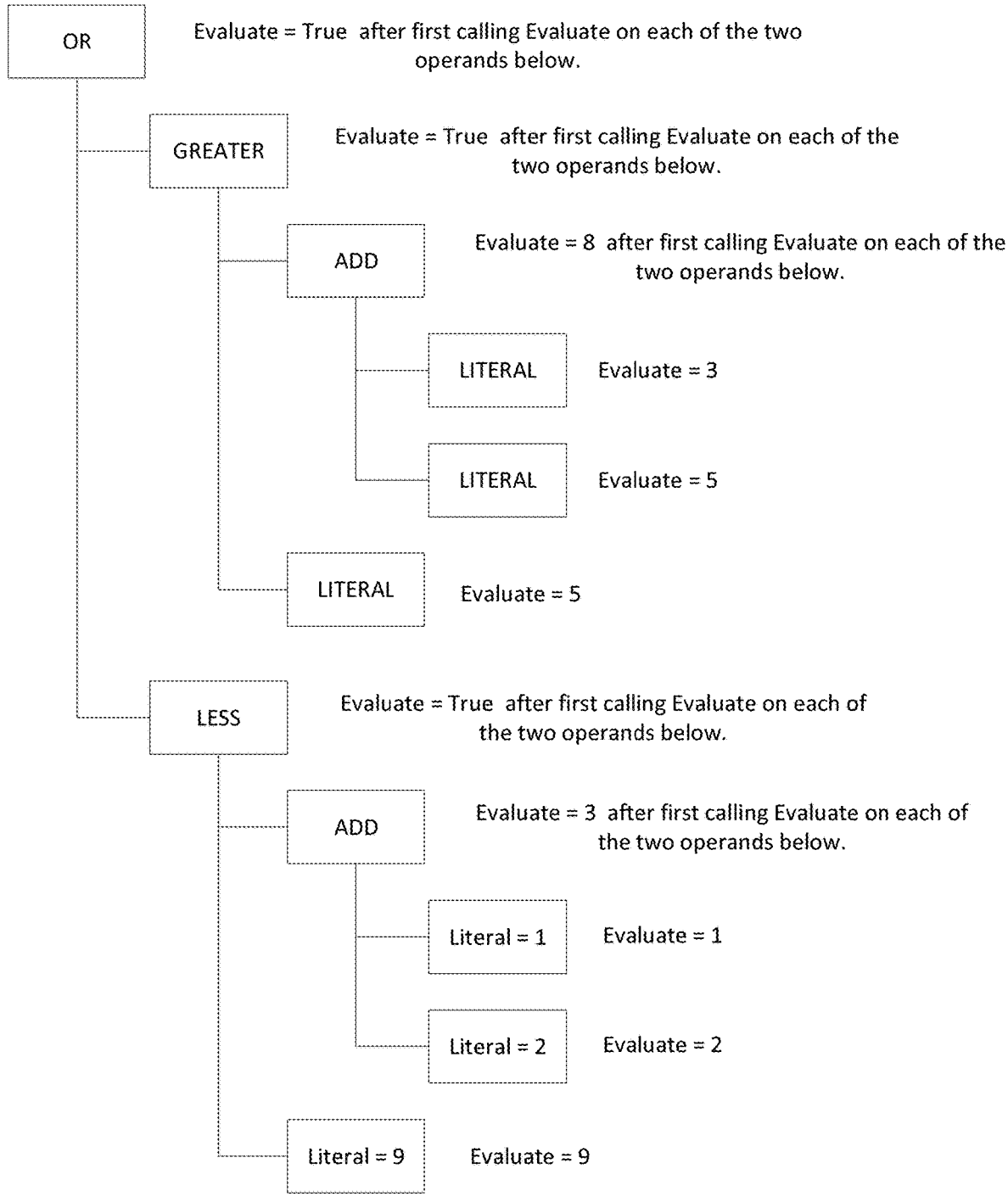
FIG. 2F illustrates another example of a strongly-typed expression tree, in accordance with some example embodiments described herein.
Figure 6:
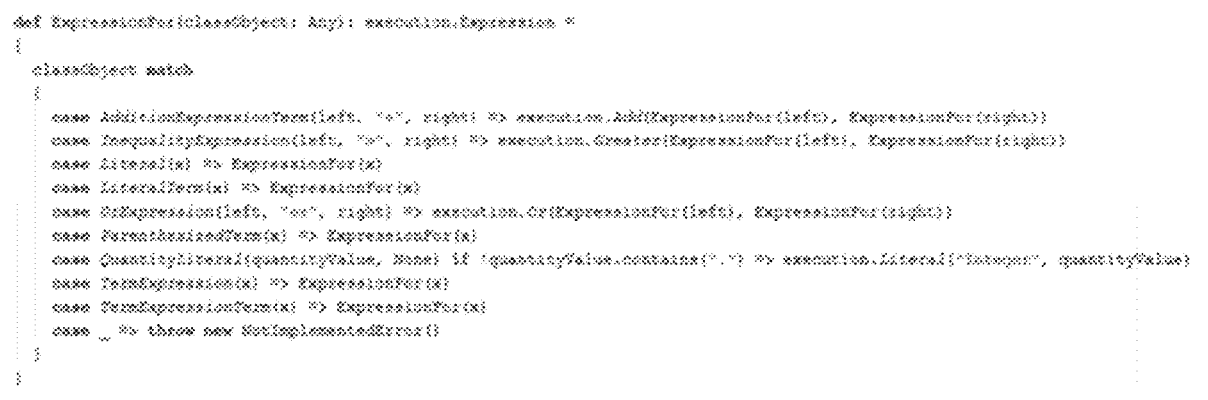

As illustrated in operation 504, the apparatus 300 includes means, such as configuration circuitry 310 or the like, for converting the abstract syntax tree into a strongly-typed expression tree. In some embodiments, this operation includes two steps. The first step may comprise evaluating nodes of the abstract syntax tree using a set of predefined mapping rules that define a correspondence between abstract syntax tree nodes and strongly-typed expression tree nodes. The second step may comprise creating the strongly-typed expression tree, wherein the strongly-typed expression tree only includes nodes from the abstract syntax tree for which a correspondence to strongly-typed expression tree nodes is defined by the set of predefined mapping rules. An example code snippet executable to perform this operation is illustrated in FIG. 6, which facilitates recursively traversing the cleaned up tree from FIGS. 2C and 2D. Each node is either passed over (if the node is deemed unnecessary) or is mapped to a node having a defined type. It should be understood that in some embodiments of the conversion from abstract syntax tree to strongly-typed expression tree, the strongly-typed expression tree that is generated has nodes consisting of either operands or literal values. Moreover, in some embodiments, performing this conversion creates a strongly typed tree of a pre-fix operation type, which means that for each operation, its child nodes are the operands needed to perform that operation. Accordingly, the mapping process gets rid of unnecessary levels in the tree. For example, FIG. 2E illustrates that the TermExpression and TermExpressionTerm levels of FIGS. 2C and 2D are eliminated (by virtue of the corresponding lines of code illustrated in FIG. 6).

In some embodiments, the first step of evaluating nodes of the abstract syntax tree includes a set of two sub-operations for each node of the abstract syntax tree. First, the interpreter identifies a type of the node. And second, the interpreter compares the identified type of the node against a set of predefined type-mapping rules that identifies a strong type corresponding to the identified type. Similarly the second step of creating the strongly-typed expression tree may be performed by the interpreter changing the type of each mapped node of the abstract syntax tree to the identified strong type. After completion of operation 504, each node is thus mapped to a strongly typed node with the appropriate operands to calculate the operation, and the structure of the tree is uniform by virtue of its pre-fix operation type. Following completion of operation 504, the procedure returns to operation 406, in which the strongly-typed expression tree is stored in a memory.

Figure 7:
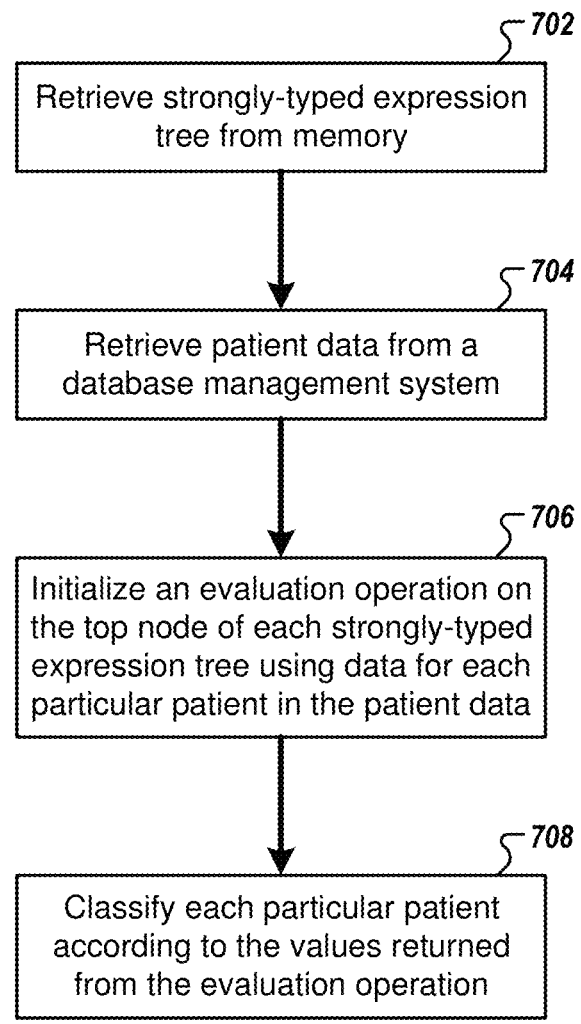
FIG. 7 illustrates a flowchart describing example operations for applying measure logic to patient data, in accordance with some example embodiments described herein.
Figure 8:
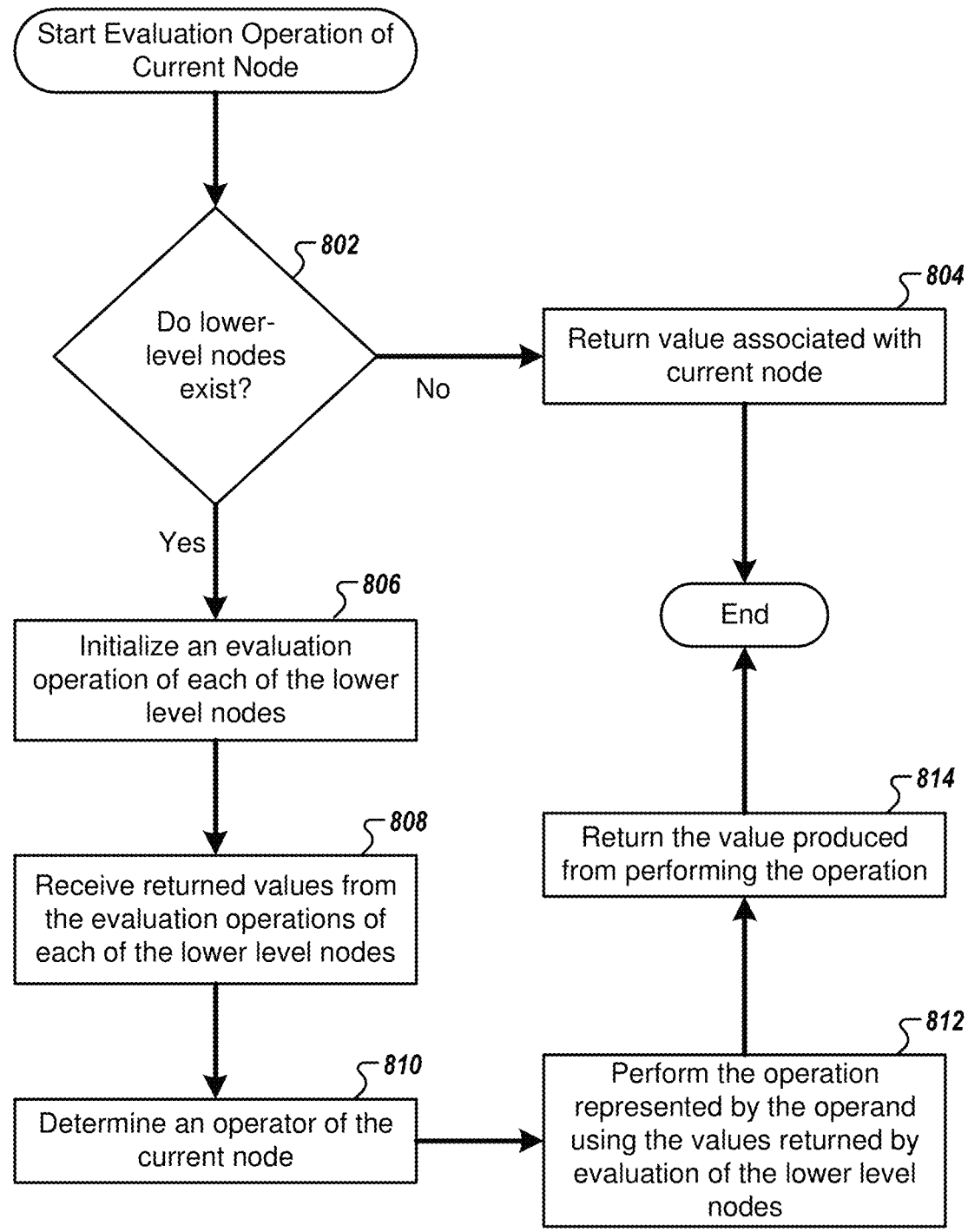
FIG. 8 illustrates a flowchart describing example operations for evaluating a value of a particular node in a strongly-typed expression tree, in accordance with some example embodiments described herein.

Operations for Utilizing Strongly-Typed Expression Trees to Generate Measure Data Turning to FIGS. 7 and 8, flowcharts are illustrated that contain operations for utilizing executable strongly-typed expression trees in connection with stored patient data to generate measures. As with the operations described in connection with FIGS. 4, 5, and 6, the operations illustrated in FIGS. 7 and 8 may be performed by, with the assistance of, and/or under the control of an interpreter embodied by apparatus 300, and more particularly through the use of one or more of processor 302, memory 304, communications circuitry 306, input/output circuitry 308, and data evaluation circuitry 312.

During the run-time stage operations of FIGS. 7 and 8, patient data will be passed into the interpreter and be used in calculations as was mentioned above. The "evaluate" function is called on the statement node (e.g., the top-node) for each strongly-typed expression tree representing a particular CQL clause. As discussed in connection with FIG. 8 below, this will initiate an operation to evaluate all operations underneath the statement node and finally come up with a result for the statement. After evaluating each strongly typed expression tree, the result will be a collection of statement results, which can be viewed as a series of key-value pairs, where each key is the statement name and the value is the evaluated result from executing the strongly-typed expression tree corresponding to that CQL statement.

It should be understood that while the operations of FIGS. 7 and 8 may be performed at a distinct and later time period (and even by a different device or set of devices) than the operations in FIGS. 4, 5, and 6, in some embodiments the generation of strongly-typed expression trees as shown in FIGS. 4, 5, and 6 is performed during the same run-time stage in which a device or set of devices performs operations described in FIGS. 7 and 8. The former embodiments streamline performance of the operations described below, while the latter embodiments provide greater flexibility to the system by avoiding the need to pre-process measures ahead of time.

As illustrated in FIG. 7, example operations are disclosed for applying measure logic to patient data. It will be understood that the operations described in connection with FIG. 7 may comprise more detailed illustrations of the high-level description illustrated at operation 408 of FIG. 4, and that following the operations described in FIG. 7, the procedure may then advance to optional operation 410.

As illustrated in operation 702, the apparatus 300 includes means, such as data evaluation circuitry 312 or the like, for retrieving a strongly-typed expression tree from memory. In some embodiments, this strongly-typed expression tree may be stored in a database by virtue of the bifurcation of the operations described in FIGS. 4 and 5 from the operations described in FIGS. 7 and 8. However, in other embodiments, these operations may all be performed together in run-time, in which case the strongly-typed expression trees corresponding to the CQL file need not be retrieved from a database, but are generated during run-time by invoking the procedure described in connection with FIGS. 4, 5, and 6 above.

As illustrated in operation 704, the apparatus 300 includes means, such as data evaluation circuitry 312 or the like, for retrieving patient data from a database management system associated with a healthcare provider. In a typical scenario, this patient data may regard the patients serviced by the healthcare provider, although in embodiments where the healthcare provider is an insurer or hospital, the patient data may regard patients serviced by third parties as well.

As illustrated in operations 706 and 708, the apparatus 300 includes means, such as data evaluation circuitry 312 or the like, for executing all of the strongly-typed expression trees corresponding to a CQL file using the retrieved patient data. Execution of each individual strongly-typed expression tree using retrieved patient data is described in greater detail below.

As illustrated in operation 706, the apparatus 300 includes means, such as data evaluation circuitry 312 or the like, for initializing an evaluation operation (or "evaluate" function, as described previously) on the top node of each strongly-typed expression tree corresponding to a single CQL statement within the CQL file. The evaluation operation uses data for each particular patient in the patient data. The sub-steps involved in each evaluation operation is described in greater detail in connection with FIG. 8 below.

Finally, as illustrated in operation 708, the apparatus 300 includes means, such as data evaluation circuitry 312 or the like, for classifying each particular patient according to the value returned from the evaluation operation of operation 706. As noted above, following operation 708, the procedure may conclude or return to optional operation 410 shown in FIG. 4 for generation of a measure report that may eventually be transmitted to CMS.

Turning next to FIG. 8, example operations are disclosed for evaluating the value of a particular node in a strongly-typed expression tree, in accordance with some example embodiments described herein. It will be understood that the operations described in connection with FIG. 8 are invoked from operation 706 of FIG. 7. Because the operations described in FIG. 8 begin with an evaluation operation of a top node of a strongly-typed expression tree, new instances of the procedure described in FIG. 8 may be called within existing instances of this procedure. In any event, following completion of the evaluation operation of the top node of a given strongly-typed expression tree, the procedure of FIG. 8 concludes.

As illustrated in operation 802, the apparatus 300 includes means, such as data evaluation circuitry 312 or the like, for evaluating whether lower-level nodes exist. This evaluation may include determining whether the data structure representing the node is terminal or not or whether it stores a value or an operator. If no lower level nodes exist, then the procedure advances to operation 804. If lower level nodes exist, however, the procedure advances to operation 806.

As illustrated in operation 804, the apparatus 300 includes means, such as data evaluation circuitry 312 or the like, for returning a value associated with the particular node. Subsequently, the instantiation of the evaluation operation ends, and the procedure returns either to a higher-level instance of the evaluation operation (e.g., operation 808) or to operation 708 of FIG. 7, if there are no higher-level instances of the evaluation operation (e.g., when the evaluation operation regards the top node of the strongly-typed expression tree). In embodiments in which additional strongly-typed expression trees have been generated in association with a CQL file, then if there are no higher-level instances of the evaluation operation (e.g., operation 808), then the apparatus 300 determines whether additional strongly-typed expression trees have yet to be evaluated. If so, then the apparatus 300 begins the procedure again with the top node of one of the not-yet-evaluated strongly-typed expression trees.

Operations 806 through 814 are reached if lower-level nodes exist. In operation 806, the apparatus 300 includes means, such as data evaluation circuitry 312 or the like, for initializing evaluation operations of each of the lower level nodes. For each such initialization, the procedure for that lower-level node begins at operation 802 and concludes after either operation 804 or 814.

As illustrated in operation 808, the apparatus 300 includes means, such as data evaluation circuitry 312 or the like, for receiving returned values from the evaluation operations of each of the lower level nodes.

As illustrated in operation 810, the apparatus 300 includes means, such as data evaluation circuitry 312 or the like, for determining an operation invoked by the particular node. This determination may include, for instance, identifying a corresponding field within a data structure representing the particular node and retrieving the value stored in that field.

As illustrated in operation 812, the apparatus 300 includes means, such as data evaluation circuitry 312 or the like, for performing the determined operation using the returned values from the evaluation operation initialized on each of the lower level nodes. This operation may be a basic arithmetic or Boolean operation.

As illustrated in operation 814, the apparatus 300 includes means, such as data evaluation circuitry 312 or the like, for returning a value produced by performing the operation.

From operation 814, the instantiation of the evaluation operation ends, and the procedure returns either to a higher-level instance of the evaluation operation (e.g., operation 808) or, if there are no higher-level instances, then the procedure concludes by returning the resulting value as the result of the corresponding CQL statement. As noted previously, if there are additional CQL statements having corresponding strongly-typed expression trees, then the apparatus 300 proceeds to invoke the procedure of FIG. 8 on each of those strongly-typed expression trees one by one until all have been evaluated. Subsequently, the procedure returns to operation 708 of FIG. 7.

As described above, example embodiments provide methods and apparatuses that facilitate efficient interpretation of CQL files and generation of corresponding strongly-typed expression trees. Example embodiments thus contemplate the use of these strongly-typed expression trees in conjunction with proprietary database management systems to efficiently populate measures for reporting. Example embodiments described herein avoid the need to manually hand-write executable code for each set of CQL-defined measure logic, which saves time and resources, while also eliminating the possibility of human error that has been unavoidable in the past. Moreover, embodiments described herein avoid the overhead of dealing with flat CQL files themselves. For instance, utilizing flat CQL files requires a process for deploying the correct CQL files to the correct servers and maintaining them there. There would need to be a folder structure established, possibly on multiple servers, that allows versioning the files, classifying them by client, etc. Moreover, this process would also need to ensure that the right files are in the right places in the right servers during run-time. In other words, because flat CQL files define an integral part of the measure definition, storing them using a file system requires additional overhead to manage them along with the rest of the measure definition (which is most likely to be in a database). Finally, embodiments that bifurcate the generation of strongly-typed expression trees from the run-time execution of the measure provide a mechanism that creates an executable and storable (e.g., persistable) expression tree in a first authoring/configuration stage, which in turn expedites the actual execution of the measure. Moreover, bifurcation of these processes enables the identification and resolution of syntax errors, file-not-found errors, or the like ahead of time, thus ensuring that these common errors, which may otherwise be encountered when attempting to read and parse CQL files at run-time, do not occur.

FIGS. 4, 5, 7, and 8 illustrate flowcharts describing the operation of apparatuses, methods, and computer program products according to example embodiments of the invention. It will be understood that each block of the flowcharts, and combinations of blocks in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory of an apparatus 300 employing an embodiment of the present invention and executed by a processor of the apparatus 300. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware and computer instructions.

In some embodiments, some of the operations above may be modified or further amplified. Furthermore, in some embodiments, additional optional operations may be included. Modifications, amplifications, or additions to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for facilitating a compilation of measure data, the method comprising:
   receiving a Clinical Quality Language (CQL) file comprising measure logic configured as machine-readable expressions, and a CQL grammar file configured to parse the CQL file, wherein the CQL file and the CQL grammar file are published by Health Level Seven (HL7) and are configured to enable reporting relating to a particular process or outcome of care;
   generating, by configuration circuitry of an interpreter, at least one abstract syntax tree based on the CQL file comprising the measure logic and the CQL grammar file;
   converting, by the configuration circuitry, the at least one abstract syntax tree into at least one strongly-typed expression tree, wherein the at least one strongly-typed expression tree comprises nodes from the at least one abstract syntax tree, based on a set of predefined mapping rules that define a correspondence between abstract syntax tree nodes and strongly-typed expression tree nodes;
   storing the at least one strongly-typed expression tree in a memory;
   retrieving patient data associated with a plurality of patients from a healthcare database;
   determining a state of each patient within the plurality of patients in a clinical measure associated with the measure logic of the CQL file by executing the at least one strongly-typed expression tree using the retrieved patient data, wherein the state of each patient comprises a position of the patient within an initial patient population, in a denominator but not in a numerator of the clinical measure, in both the denominator and numerator of the clinical measure, or outside both the denominator and numerator of the clinical measure, wherein the denominator of the clinical measure represents a subset of the patient population defining a group of patients that the clinical measure is designed to address, and the numerator of the clinical measure defines a subset of the group of patients for whom the particular process or outcome of care occurs;
   generating a measure report comprising classification data regarding each patient based on the determination; and
   transmitting the measure report to a remote administrator of healthcare services.

2. The method of claim 1, further comprising, for a particular abstract syntax tree of the at least one abstract syntax tree:
   pruning, by the configuration circuitry, non-pertinent information from each node of the particular abstract syntax tree, wherein non-pertinent information comprises information unrelated to node type or node value,
   wherein of converting the particular abstract syntax tree into a corresponding strongly-typed expression tree is performed after pruning all non-pertinent information from each node of the particular abstract syntax tree.

3. The method of claim 1, wherein converting a particular abstract syntax tree of the at least one abstract syntax tree into a corresponding strongly-typed expression tree further comprises:
   evaluating, by the configuration circuitry, one or more nodes of the particular abstract syntax tree using the set of predefined mapping rules that define the correspondence between abstract syntax tree nodes and strongly-typed expression tree nodes.

4. The method of claim 1, further comprising:
   retrieving the at least one strongly-typed expression tree from the memory; and
   causing transmission of the measure report to a third party.

5. The method of claim 4, wherein executing a particular strongly-typed expression tree using the received patient data comprises:
   initializing an evaluation operation on a top node of the particular strongly-typed expression tree using data for each particular patient identified by the patient data,
   wherein the evaluation operation of a particular node of the particular strongly-typed expression tree initiates an evaluation on all lower level nodes underneath the particular node of the particular strongly-typed expression tree.

6. The method of claim 5, wherein the evaluation operation of a particular node comprises:
evaluating if one or more lower-level nodes exist;
in an instance in which one or more lower-level nodes do not exist, returning a value associated with the particular node; and
in an instance in which at least one lower level node exists,
initializing an evaluation operation of each lower level node,
receiving returned values from the evaluation operations of each lower level node,
determining an operation represented by the particular node,
performing the operation using the returned values from the evaluation operation initialized on each lower level node, and
returning a value produced by performing the operation.

7. An apparatus for facilitating a compilation of measure data, the apparatus comprising at least one processor and at least one memory storing computer-executable instructions, that, when executed by the at least one processor, cause the apparatus to:
receive a Clinical Quality Language (CQL) file comprising measure logic configured as machine-readable expressions, and a CQL grammar file configured to parse the CQL file, wherein the CQL file and the CQL grammar file are published by Health Level Seven (HL7) and are configured to enable reporting relating to a particular process or outcome of care;
generate, by configuration circuitry of an interpreter, at least one abstract syntax tree based on the CQL file comprising the measure logic and the CQL grammar file;
convert the at least one abstract syntax tree into at least one strongly-typed expression tree, wherein the at least one strongly-typed expression tree comprises fewer nodes than the at least one abstract syntax tree;
store the at least one strongly-typed expression tree in a memory;
retrieve patient data associated with a plurality of patients from a healthcare database;
determine a state of each patient within the plurality of patients in a clinical measure associated with the measure logic of the CQL file by executing the at least one strongly-typed expression tree using the retrieved patient data, wherein the state of each patient comprises a position of the patient within an initial patient population, in a denominator but not in a numerator of the clinical measure, in both the denominator and numerator of the clinical measure, or outside both the denominator and numerator of the clinical measure, wherein the denominator of the clinical measure represents a subset of the patient population defining a group of patients that the clinical measure is designed to address, and the numerator of the clinical measure defines a subset of the group of patients for whom the particular process or outcome of care occurs;
generate a measure report comprising classification data regarding each patient based on the determination; and
transmit the measure report to a remote administrator of healthcare services.

8. The apparatus of claim 7, wherein the computer-executable instructions, when executed by the at least one processor, further cause the apparatus to, for a particular abstract syntax tree of the at least one abstract syntax tree:
prune non-pertinent information from each node of the particular abstract syntax tree, wherein non-pertinent information includes information unrelated to node type or node value,
wherein the computer-executable instructions, when executed by the at least one processor, cause the apparatus to convert the particular abstract syntax tree into a corresponding strongly-typed expression tree after pruning all non-pertinent information from each node of the particular abstract syntax tree.

9. The apparatus of claim 7, wherein the computer-executable instructions, when executed by the at least one processor, cause the apparatus to convert a particular abstract syntax tree of the at least one abstract syntax tree into a corresponding strongly-typed expression tree by causing the apparatus to:
evaluate one or more nodes of the particular abstract syntax tree using the set of predefined mapping rules that define the correspondence between abstract syntax tree nodes and strongly-typed expression tree nodes.

10. The apparatus of claim 9, wherein the corresponding strongly-typed expression tree is structured as a prefix kind of tree.

11. The apparatus of claim 7, wherein the computer-executable instructions, when executed by the at least one processor, further cause the apparatus to:
retrieve the at least one strongly-typed expression tree from the memory; and
cause transmission of the measure report to a third party.

12. The apparatus of claim 11, wherein the computer-executable instructions, when executed by the at least one processor, cause the apparatus to execute the particular strongly-typed expression tree using the received patient data by causing the apparatus to:
initialize an evaluation operation on a top node of the particular strongly-typed expression tree using data for each particular patient identified by the patient data,
wherein the evaluation operation of any particular node of the particular strongly-typed expression tree initiates an evaluation on all lower level nodes underneath the particular node of the particular strongly-typed expression tree.

13. The apparatus of claim 12, wherein the evaluation operation of a particular node comprises:
evaluating if one or more lower-level nodes exist;
in an instance in which one or more lower-level nodes do not exist, returning a value associated with the particular node; and
in an instance in which at least one lower level node exists,
initializing evaluation operations of each lower level node,
receiving returned values from the evaluation operations of each lower level node,
determining an operation represented by the particular node,
performing the operation using the returned values from the evaluation operation initialized on each lower level node, and
returning a value produced by performing the operation.

14. A computer program product comprising at least one non-transitory computer-readable storage medium for facilitating a compilation of measure data, the at least one non-transitory computer-readable storage medium storing computer-executable instructions that, when executed, cause an apparatus to:

receive a Clinical Quality Language (CQL) file comprising measure logic configured as machine-readable expressions, and a CQL grammar file configured to parse the CQL file, wherein the CQL file and the CQL grammar file are published by Health Level Seven (HL7) and are configured to enable reporting relating to a particular process or outcome of care;

generate, by configuration circuitry of an interpreter, at least one abstract syntax tree based on the CQL file comprising the measure logic and the CQL grammar file;

convert the at least one abstract syntax tree into at least one strongly-typed expression tree, wherein the at least one strongly-typed expression tree comprises nodes from the at least one abstract syntax tree, based on a set of predefined mapping rules that define a correspondence between abstract syntax tree nodes and strongly-typed expression tree nodes;

store the at least one strongly-typed expression tree in a memory;

retrieve patient data associated with a plurality of patients from a healthcare database;

determine a state of each patient within the plurality of patients in a clinical measure associated with the measure logic of the CQL file by executing the at least one strongly-typed expression tree using the retrieved patient data, wherein the state of each patient comprises a position of the patient within an initial patient population, in a denominator but not in a numerator of the clinical measure, in both the denominator and numerator of the clinical measure, or outside both the denominator and numerator of the clinical measure, wherein the denominator of the clinical measure represents a subset of the patient population defining a group of patients that the clinical measure is designed to address, and the numerator of the clinical measure defines a subset of the group of patients for whom the particular process or outcome of care occurs;

generate a measure report comprising classification data regarding each patient based on the determination; and transmit the measure report to a remote administrator of healthcare services.

15. The computer program product of claim 14, wherein the computer-executable instructions, when executed, cause the apparatus to convert a particular abstract syntax tree of the at least one abstract syntax tree into a corresponding strongly-typed expression tree by causing the apparatus to:

evaluate one or more nodes of the particular abstract syntax tree using a set of predefined mapping rules that define a correspondence between abstract syntax tree nodes and strongly-typed expression tree nodes.

16. The computer program product of claim 15, wherein the corresponding strongly-typed expression tree is structured as a prefix kind of tree.

17. The computer program product of claim 14, wherein the computer-executable instructions, when executed, further cause the apparatus to:

retrieve the at least one strongly-typed expression tree from the memory; and cause transmission of the measure report to a third party.

18. The computer program product of claim 17, wherein the computer-executable instructions, when executed, cause the apparatus to execute the particular strongly-typed expression tree using the received patient data by causing the apparatus to:

initialize an evaluation operation on a top node of the particular strongly-typed expression tree using data for each particular patient identified by the patient data, wherein the evaluation operation of any particular node of the particular strongly-typed expression tree initiates an evaluation on all lower level nodes underneath the particular node of the particular strongly-typed expression tree.

19. The computer program product of claim 18, wherein the evaluation operation of a particular node comprises:

evaluating if one or more lower-level nodes exist;

in an instance in which one or more lower-level nodes do not exist, returning a value associated with the particular node; and in an instance in which at least one lower level node do exists, initializing evaluation operations of each lower level node, receiving returned values from the evaluation operations of each lower level node, determining an operation represented by the particular node, performing the operation using the returned values from the evaluation operation initialized on each lower level node, and returning a value produced by performing the operation.

* * * * *